US 9,953,731 B2

(12) United States Patent
Buchmeyer

(10) Patent No.: US 9,953,731 B2
(45) Date of Patent: Apr. 24, 2018

(54) RADIATION PROTECTION ARRANGEMENT

(71) Applicant: MAVIG GMBH, Munich (DE)

(72) Inventor: Markus Buchmeyer, Munich (DE)

(73) Assignee: MAVIG GMBH, Munich (DE)

( * ) Notice: Subject to any disclaimer, the term of this patent is extended or adjusted under 35 U.S.C. 154(b) by 57 days.

(21) Appl. No.: 15/151,701

(22) Filed: May 11, 2016

(65) Prior Publication Data

US 2016/0336085 A1 Nov. 17, 2016

(30) Foreign Application Priority Data

May 12, 2015 (DE) .......................... 10 2015 208 829

(51) Int. Cl.
*G21F 3/00* (2006.01)
*A61B 6/10* (2006.01)

(52) U.S. Cl.
CPC ............... *G21F 3/00* (2013.01); *A61B 6/107* (2013.01)

(58) Field of Classification Search
CPC .... G21K 1/00; G21K 1/10; G21F 1/00; G21F 1/10; G21F 3/00; G21F 7/00; A61B 6/107; A61B 6/10; A61B 6/06; A61B 6/04
See application file for complete search history.

(56) References Cited

U.S. PATENT DOCUMENTS

| 4,062,518 A | 12/1977 | Stivender et al. |
| 5,006,718 A * | 4/1991 | Lenhart .................. A61B 6/107 250/515.1 |

(Continued)

FOREIGN PATENT DOCUMENTS

| DE | 1466848 | 2/1969 |
| DE | 1516420 A1 | 8/1969 |

(Continued)

OTHER PUBLICATIONS

EP Search Report dated Feb. 10, 2017 issued in corresponding European Patent Appln. No. 16168930.2.

(Continued)

*Primary Examiner* — David E Smith
(74) *Attorney, Agent, or Firm* — Scully Scott Murphy and Presser; Frank Digiglio

(57) ABSTRACT

The present invention relates to a radiation protection arrangement, in particular for attachment to a support rail, which is attached to a side of a treatment table, comprising: a holder on which a radiation protection drape is arranged, wherein the holder is attachable to the support rail and comprises a fastening means with which the holder can be fastened to the support rail. The fastening means is formed on a side of the holder and comprises at least one first bracket part and at least one second bracket part. The first and the second bracket parts each have an L-shaped profile with a first leg and a second leg, wherein the first and the second bracket parts are arranged such that the first legs are aligned in parallel and the second legs face each other. The first bracket part is arranged at an upper edge of the holder and the second bracket part is arranged at the lower edge of the holder. Consequently, the first bracket part is arranged relative to a longitudinal direction of the holder at a first distance from the second bracket part such that the holder in a first position in which the holder is pivoted relative to the support rail can be brought into contact with the support rail. With a pivoting motion the holder can be brought into a second position in which the holder is fastened to the support rail.

11 Claims, 7 Drawing Sheets

(56) References Cited

U.S. PATENT DOCUMENTS

Figure 1:
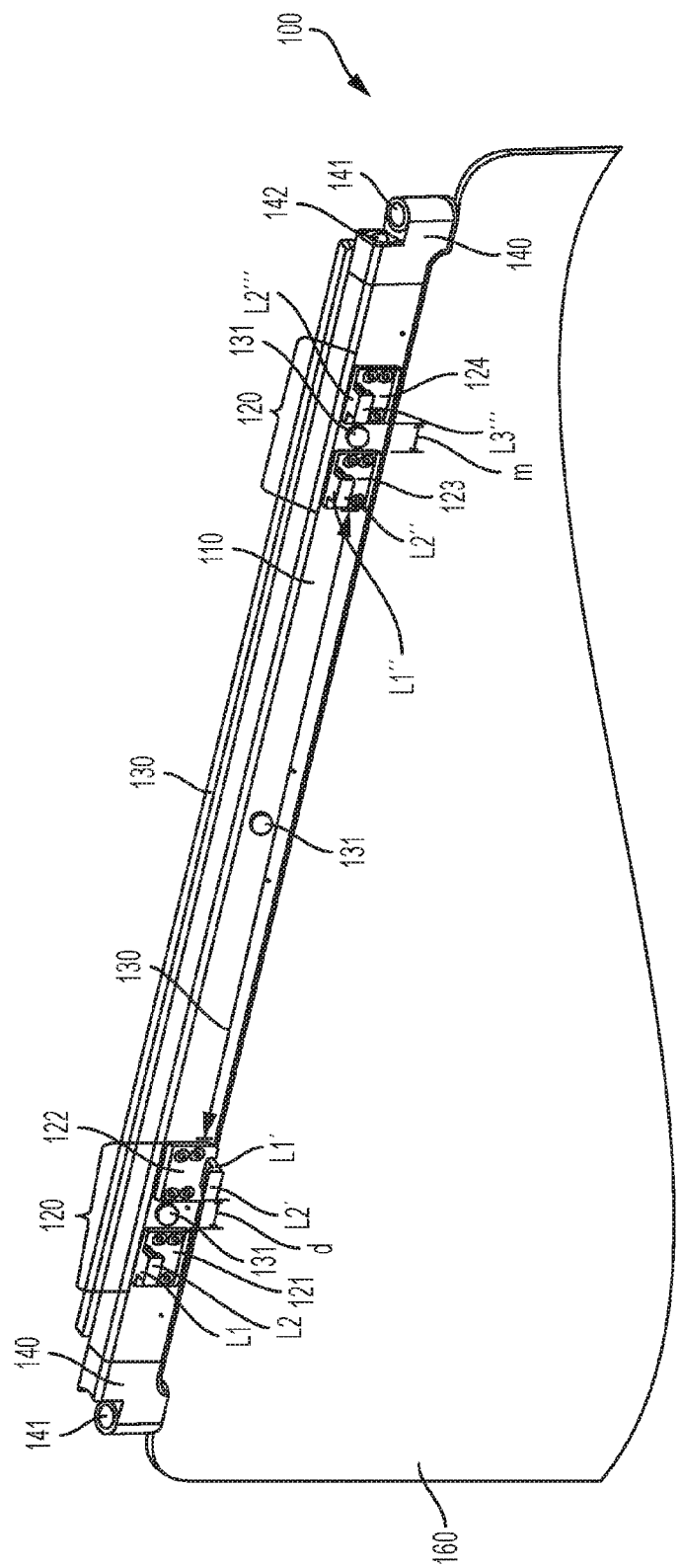

| | | | | |
|---|---|---|---|---|
| 5,900,638 A | * | 5/1999 | Jaeger | A61B 6/107 250/515.1 |
| 2009/0020713 A1 | * | 1/2009 | Baudro | G21F 1/085 250/517.1 |
| 2014/0048730 A1 | | 2/2014 | Niedzielski | |
| 2015/0272519 A1 | | 10/2015 | Buchmeyer | |

FOREIGN PATENT DOCUMENTS

| | | |
|---|---|---|
| DE | 2749826 A1 | 5/1978 |
| DE | 3012463 C2 | 10/1981 |
| DE | 29704613 U1 | 7/1997 |
| DE | 102009025380 A1 | 12/2010 |
| DE | 102012218391 A1 | 4/2014 |
| GB | 2461569 A | 1/2010 |
| WO | WO 2004/107979 A1 | 12/2004 |
| WO | 2009/124094 A2 | 10/2010 |
| WO | 2014/167544 A2 | 10/2014 |

OTHER PUBLICATIONS

English Abstract of WO 101146109 A1, dated Dec. 23, 2010.
English Abstract of DE3046532 A1, dated Oct. 8, 1981.
EP Search Report dated Oct. 11, 2016 issued in corresponding European Patent Appln. No. 16 16 8930.
Chinese Office Action dated May 24, 2017 issued in corresponding Chinese Patent Appln. No. 201610312539.

* cited by examiner

RADIATION PROTECTION ARRANGEMENT

The present invention relates to a radiation protection arrangement, in particular for attachment to a support rail which is attached to the side of a treatment table. The present radiation protection arrangement is especially suitable for use in interventional radiology and is used during operations for protecting the personnel involved, such as the doctor or assistant, from radiation, in particular X-ray radiation.

DE 10 2012 218 391 A1 relates to a radiation protection arrangement, in particular for attachment to a support rail which is attached to the side of a treatment table. The radiation protection arrangement comprises at least a pivotably mounted handle and a locking mechanism suitable for locking the holder on the support rail, and wherein the locking mechanism can be actuated by a pivoting motion of the at least one handle that is pivotably mounted on the holder.

DE 10 2009 025 380 A1 relates to a radiation protection arrangement, in particular for attachment to a support rail that is attached to the side of a treatment table. The radiation protection arrangement comprises at least one lamella made of a radiation protection material as well as an associated fastening device. The lamella is fastened to the fastening device so as to be able to swivel. The fastening device comprises a holder which can be placed on the support rail, and the holder can be fastened to the support rail by means of a locking device.

WO 2004/107979 relates to a radiation protection arrangement which can be attached to the side of a medical examination or treatment table as lower body protection. In one embodiment, this radiation protection arrangement comprises a plurality of lamellae arranged next to each other, which at one end are attached to a common carrier element. There is further provided an upper part which can be attached to the support rail on the treatment table. In this known radiation protection arrangement, the lamellae may consist of a lead rubber mat, which, for example, comprise lead foils embedded in PVC. The lead rubber mats are inserted in wrapping consisting of a material that can be easily cleaned and sterilized. The lamellae are variable in length by turning up a lower end and fixing this end in the turned-up position, for example by means of push buttons, hook and loop fastener or by the use of straps.

DE 1 516 420 describes a radiation protection arrangement comprising a plurality of individual lead rubber flaps which are pivotably mounted. Each lead rubber flap is pivotably mounted about an axis that is vertical to it and located above its center of gravity. One embodiment comprises a comb-like carrier provided with extensions having pins on which the individual lead rubber flaps are pivotably mounted.

DE 1 466 848 describes a radiation protection arrangement wherein lead rubber flaps are attached through rotary axes to the side edge of the carrier of a luminescent screen.

DE 27 49 826 A1 describes an X-ray shielding device comprising lead rubber panels that are pivotably mounted with brackets about axes. In one embodiment, a sliding rail has a T-shaped inner profile into which holders can be inserted.

DE 30 12 463 C2 shows a radiation protection device wherein lead rubber flaps are pivotably suspended at a carrier. In one embodiment, a support element comprises comb-like extensions on which the lead rubber flaps are articulated.

DE 297 04 613 U1 describes a radiation protection device wherein individual lead rubber straps can be pivotably arranged on a rail. In one embodiment, a carrier is provided for each lead rubber strap, which carrier is adjustably mounted in a guide rail. The lead rubber straps are pivotably mounted on a carrier about a transverse axis. Furthermore, brake means are provided preventing that the carriers unintentionally slide in the rail. Alternatively, a catch or lock may be used. In a further embodiment, each lead rubber strap has an eyelet with a through opening, on which the lead rubber flap is held by a swiveling axis.

The present invention is directed to a radiation protection arrangement which can be easily attached to a treatment table and which can be easily managed. Furthermore, the present invention is directed to a radiation protection arrangement which can be easily connected with further radiation protection arrangements, and wherein the radiation protection arrangements remain in a predefined position to each other even when the treatment table is in a slanted position.

The present invention is based on the basic idea of fastening a radiation protection arrangement with an associated holder and a corresponding fastening device by a corresponding pivoting motion on a support rail of the treatment table, and thus to ensure both a simple attachment of the radiation protection arrangements to the treatment table and a firm seat in the fastened state. Here, the invention has the advantage that the firm positioning of the radiation protection arrangement on the support rail can be quickly and safely realized and that the radiation protection arrangement need not be set down for said positioning but can be securely attached to the treatment table and/or a support rail of the treatment table by a pivoting motion that is easy to perform.

The invention is further based on the basic idea of providing a radiation protection arrangement with a part of an articulated joint, to which a further radiation protection arrangements with a further part of the articulated joint can be attached so that the two parts of the articulated joint form an articulate joint having multiple lock-in positions.

In view of the articulated joint having multiple lock-in positions, the interlinked radiation protection arrangements are firmly positioned relative to each other even when the treatment table is in a tilted position; moreover, it is also possible to prevent a change in position of the radiation protection arrangement by unintentional jolting of one or more radiation protection arrangements by providing an articulated joint comprising multiple lock-in positions.

The present invention relates to a radiation protection arrangement, in particular for attachment to a support rail, which is attached to a side of a treatment table, comprising: a holder on which a radiation protection drape is arranged, wherein the holder can be placed on the support rail and comprises a fastening means with which the holder can be fastened to the support rail. The fastening means is formed on a side of the holder and comprises at least a first bracket part and at least a second bracket part. The first and the second bracket parts each have an L-shaped profile with a first leg and a second leg, wherein the first and the second bracket parts are arranged such that the first legs are aligned in parallel and the second legs face each other. The first bracket part is arranged at an upper edge of the holder and the second bracket part is arranged at a lower edge of the holder. Consequently, relative to a longitudinal direction of the holder, the first bracket part is arranged at a first distance from the second bracket part in such a way that the holder, in a first position in which the holder is pivoted relative to the support rail, can be brought into contact with the support rail. With a pivoting motion, the holder can be brought into a second position in which the holder is fastened on the support rail.

According to an embodiment of the present invention, the fastening means comprises a third bracket part. Preferably, the third bracket part is arranged in longitudinal direction of the holder at a second distance from the second bracket part. Preferably, the second distance is n times greater than the first distance and particularly preferably n is in the range of from 1.5 to 30.

According to an embodiment of the present invention, the third bracket part has an L-shaped profile and/or comprises a fixing device.

According to an embodiment of the present invention, the fastening means comprises a fourth bracket part. Preferably, the fourth bracket part is arranged in longitudinal direction of the holder at a third distance from the bracket part. Preferably, the third distance is m times greater than the first distance and particularly preferably m is in the range of from 0.5 to 15.

According to an embodiment of the present invention, the fourth bracket part has an L-shaped profile and/or comprises a fixing means.

According to an embodiment of the present invention, each of the L-shaped profiles of the third and fourth bracket parts—provided the third and fourth bracket parts each have an L-shaped profile—has a first and a second leg, wherein the third and the fourth bracket parts are arranged such that the first legs of the third and fourth bracket parts are aligned in parallel and the second legs of the third and fourth bracket parts point in the same direction, and that the third and fourth bracket parts are arranged such that, in the fitted state, the first legs of the third and fourth bracket parts rest on the support rail.

Preferably, a supporting pad is provided at the first leg of at least one bracket part, which is arranged such that it rests on the support rail of the treatment table in the fastened state of the radiation protection arrangement at the treatment table. The supporting pad preferably contains at least one of the following materials: rubber, plastics, polyamide, PTFE, PBT, polybutyleneterephthalate, polyphenylenesulfide, aramide.

According to an embodiment of the present invention, the holder further comprises an additional rail which is attached at the side opposite to the fastening device.

The invention also relates to a radiation protection arrangement, in particular for attachment to a support rail, which is attached to a side of a treatment table, comprising: a holder on which a radiation protection drape is arranged, the holder having a long side and a short side. A first part of an articulated joint is arranged at the short side of the holder which has a bore and a pressing device and is suitable for being brought into contact with a second part of the articulated joint having a bolt and a head with at least one recess in such a way that the bolt of the second part is inserted into the bore of the first part and the pressing device of the first part is located at least in part in the at least one recess so that the first and the second part form an articulated joint having a plurality of lock-in positions.

The pressing device is preferably a ball-ended thrust screw or the pressing device has a ball-ended thrust screw. Preferably, the pressing device has a ball. Preferably, the pressing device has a spring element.

Preferably the bore has a bushing, particularly preferably a plain bearing bushing.
Preferably, the bushing and/or the plain bearing bushing is made of at least one of the following materials: bronze, in particular sintered bronze, aluminum, polyamide, PTFE, PBT, polybutyleneterephthalate, polyphenylenesulfide, aramide.

Preferably, the bolt of the second part of the articulated joint can be inserted into the bore of the first part of the articulated joint. Preferably, the at least one recess of the head of the second part of the articulated joint is designed such that the pressing device is received by the at least one recess through insertion of the bolt into the bore.

The present invention also relates to a radiation protection arrangement, in particular for attachment to a support rail, which is attached to a side of a treatment table, comprising: a holder on which a radiation protection drape is arranged, the holder having a long side and a short side. A second part of an articulated joint is arranged at the short side, which has a bolt and a head with at least one recess, and is suitable for being brought into contact with a first part part of an articulated joint having a bore and a pressing device in such a way that the bolt of the second part is inserted into the bore of the first part and the pressing device of the first part is arranged at least in part in the at least one recess so that the first and the second part form an articulated joint having a plurality of lock-in positions.

According to an embodiment of the invention, the head has at least two recesses. Preferably, there is a predefined angle between a first lock-in position in which the pressing device is arranged in a first recess and a second lock-in position in which the pressing device is arranged in a second recess. Preferably, the angle is 30°.

Preferably, the pressing device can be moved from the first into the second lock-in position by applying a predefined force acting on the first part. Preferably, the pressing device has a spring element for this purpose. In other words, the pressing device can be moved from a first into a second lock-in position by twisting the articulated joint against a predefined force.

According to an embodiment of the invention, the head has several recesses. Preferably, a predefined angle lies between the first lock-in position and the last lock-in position. Preferably, the angle is 180°.

According to an embodiment of the invention, the holder has a long and at least one short side, wherein a first or a second part of an articulated joint according to any one of the above embodiments and examples is arranged at the short side. According to an embodiment of the invention, the holder has a long and two short sides, wherein a first or a second part of an articulated joint according to any one of the above embodiments and examples is arranged at least at one of the short sides.

The present invention also relates to an articulated joint with a plurality of lock-in positions, preferably for connecting a first and a second radiation protection arrangement, with the articulated joint having a first and a second part. The first part has a bore and a pressing device and the second part has a bolt and a head with at least one recess. The first part and the second part can be connected such that the bolt of the second part is inserted into the bore of the first part and the pressing device of the first part is arranged at least in part in the at least one recess.

In the following, the invention will be discussed in detail on the basis of examples and the drawing.

Figure 2:
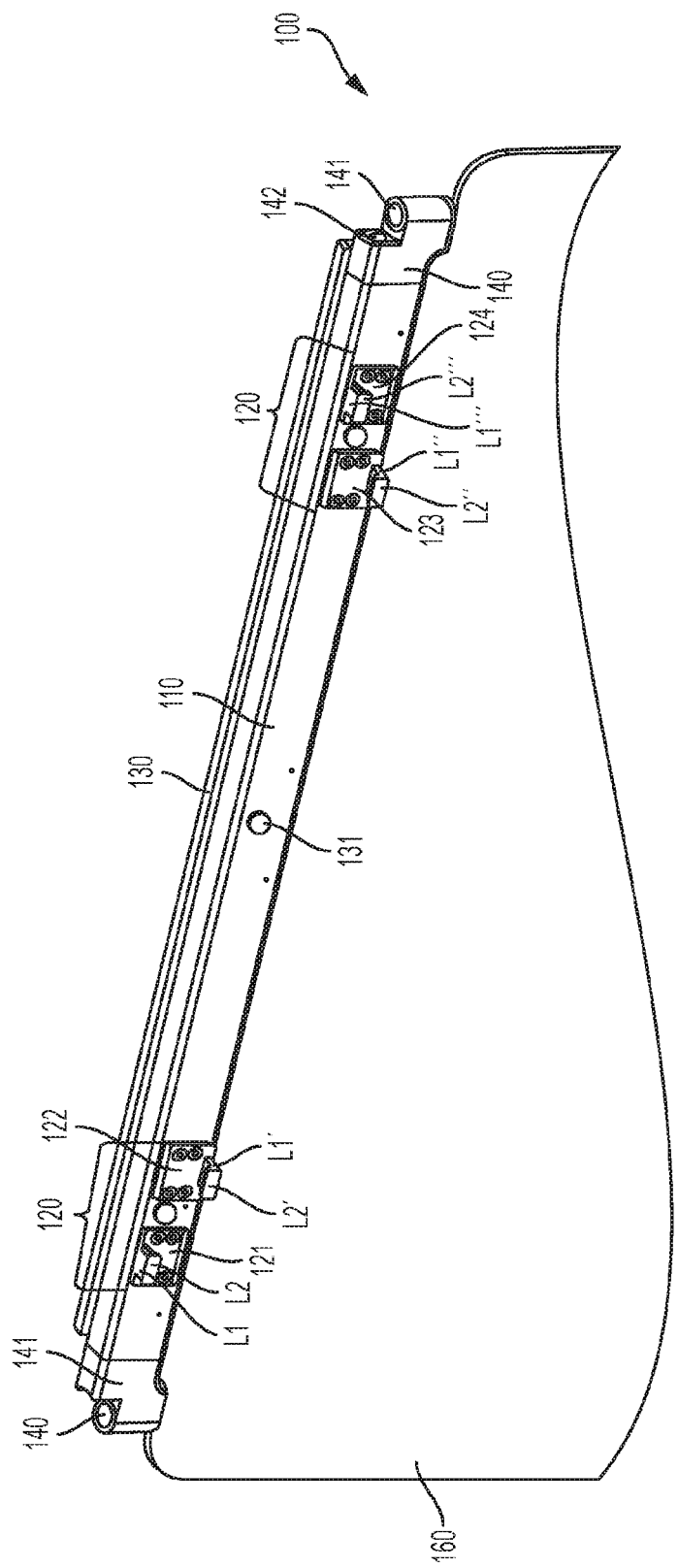
Figure 3:
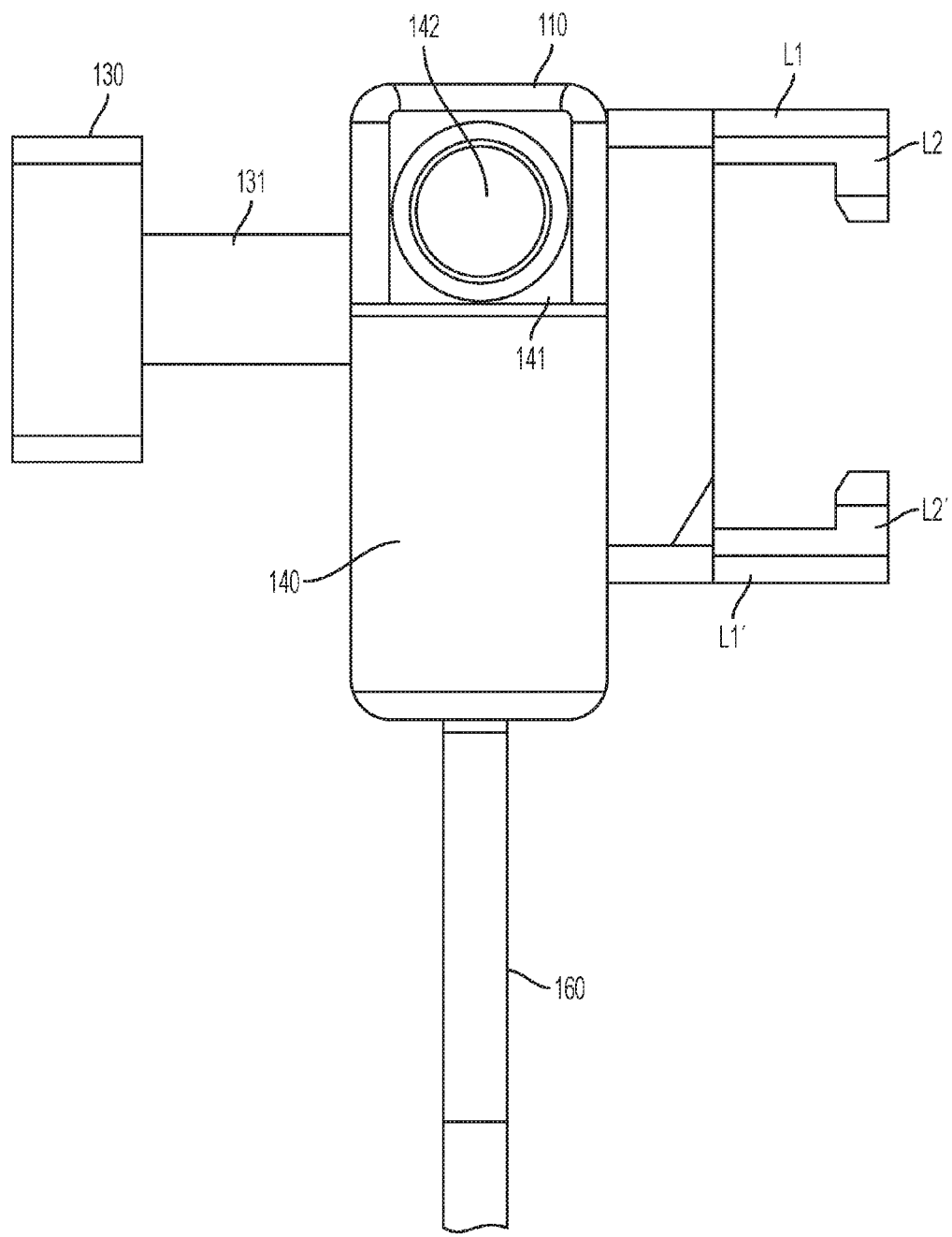
Figure 4:
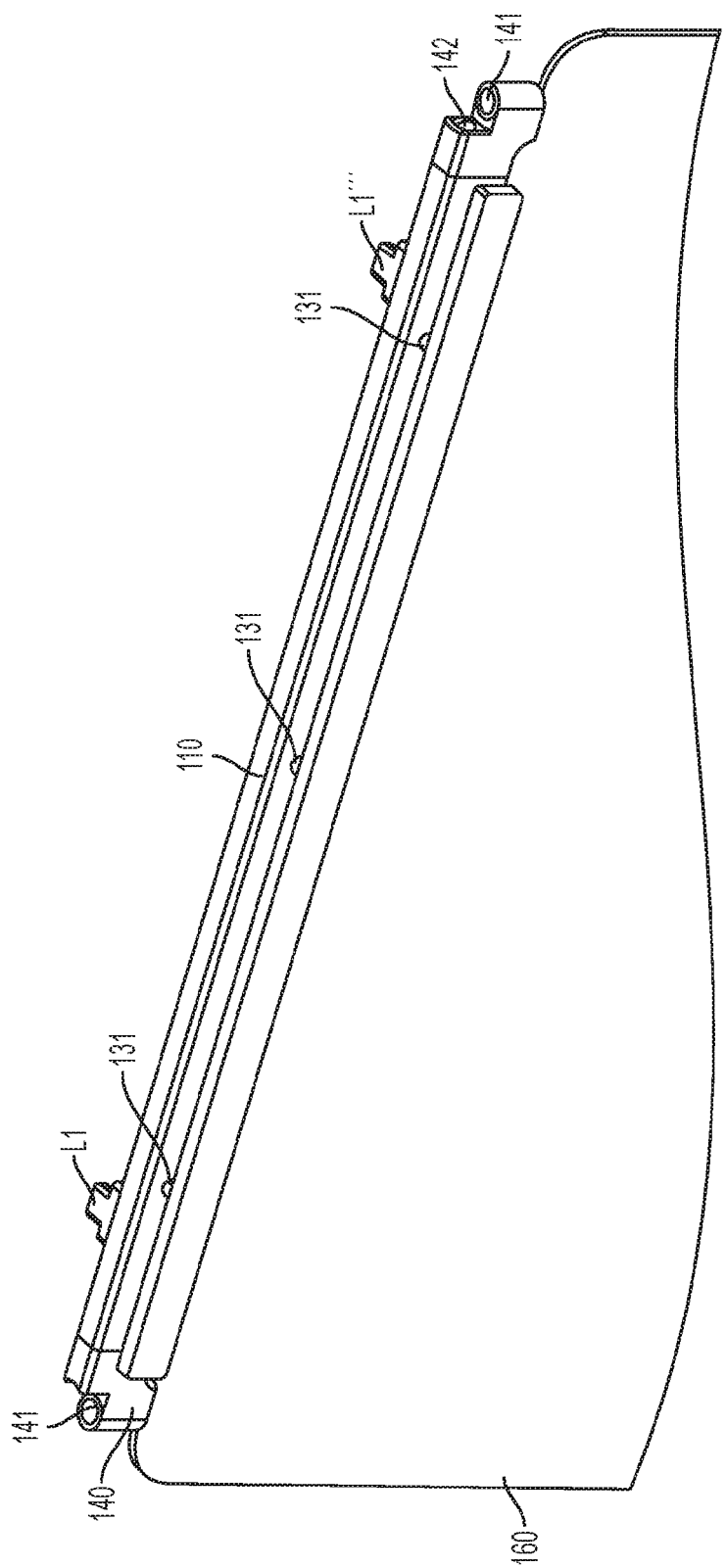
Figure 5:
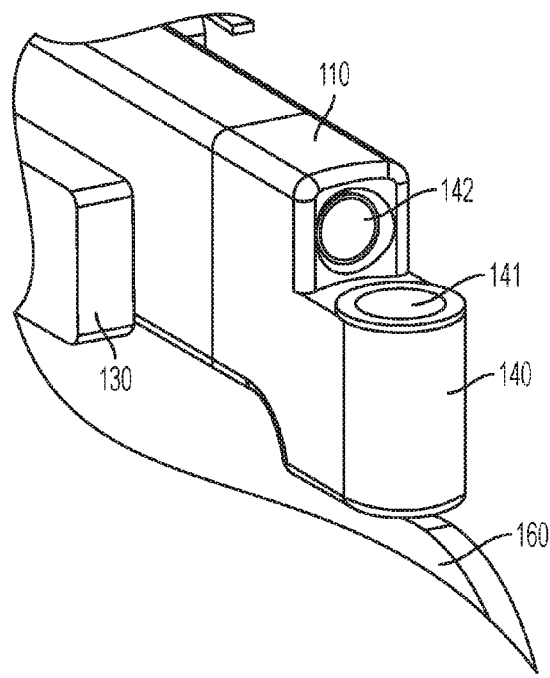
Figure 6:
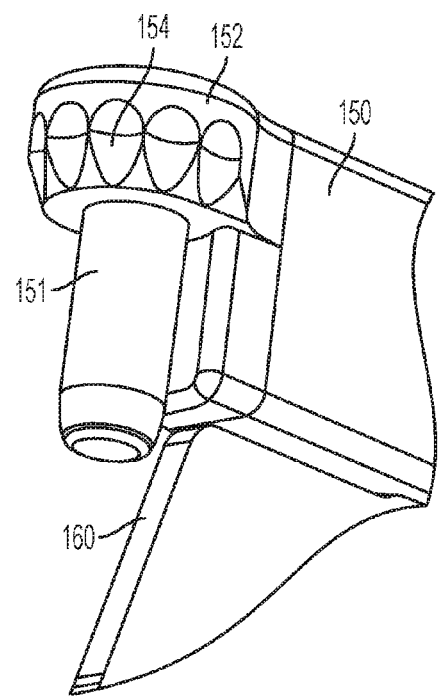
Figure 7:
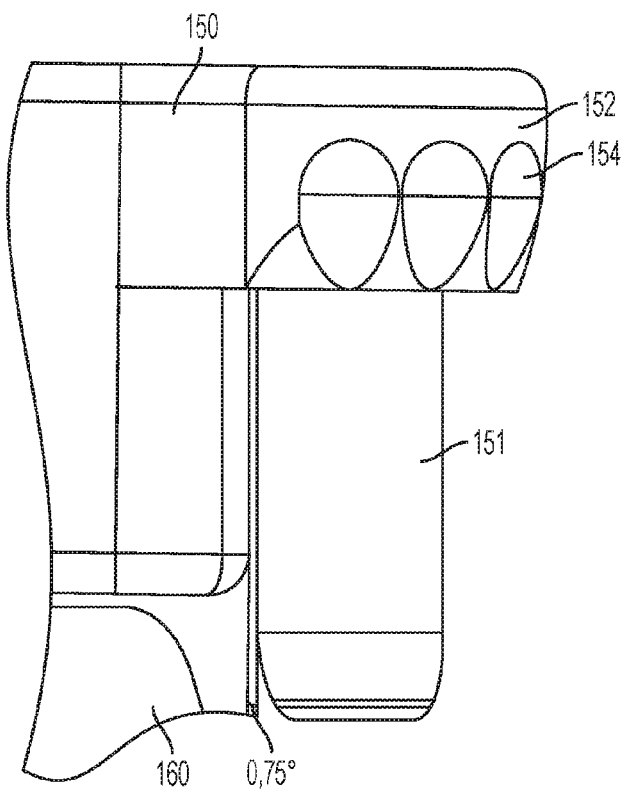
Figure 8:
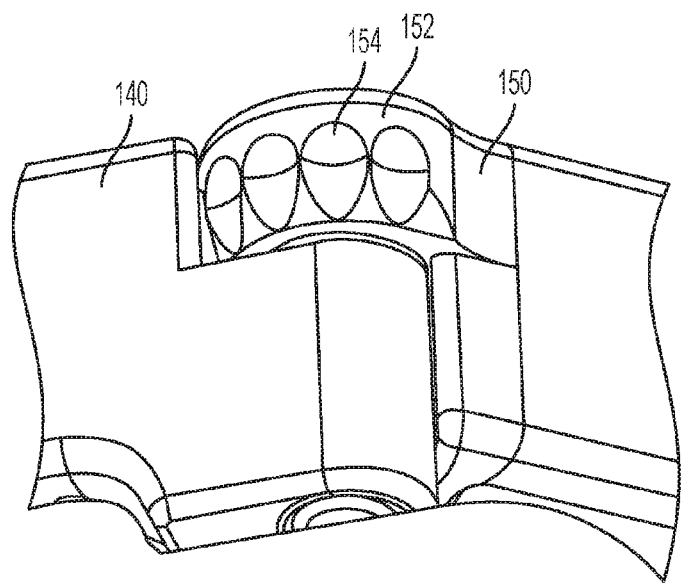
Figure 9:
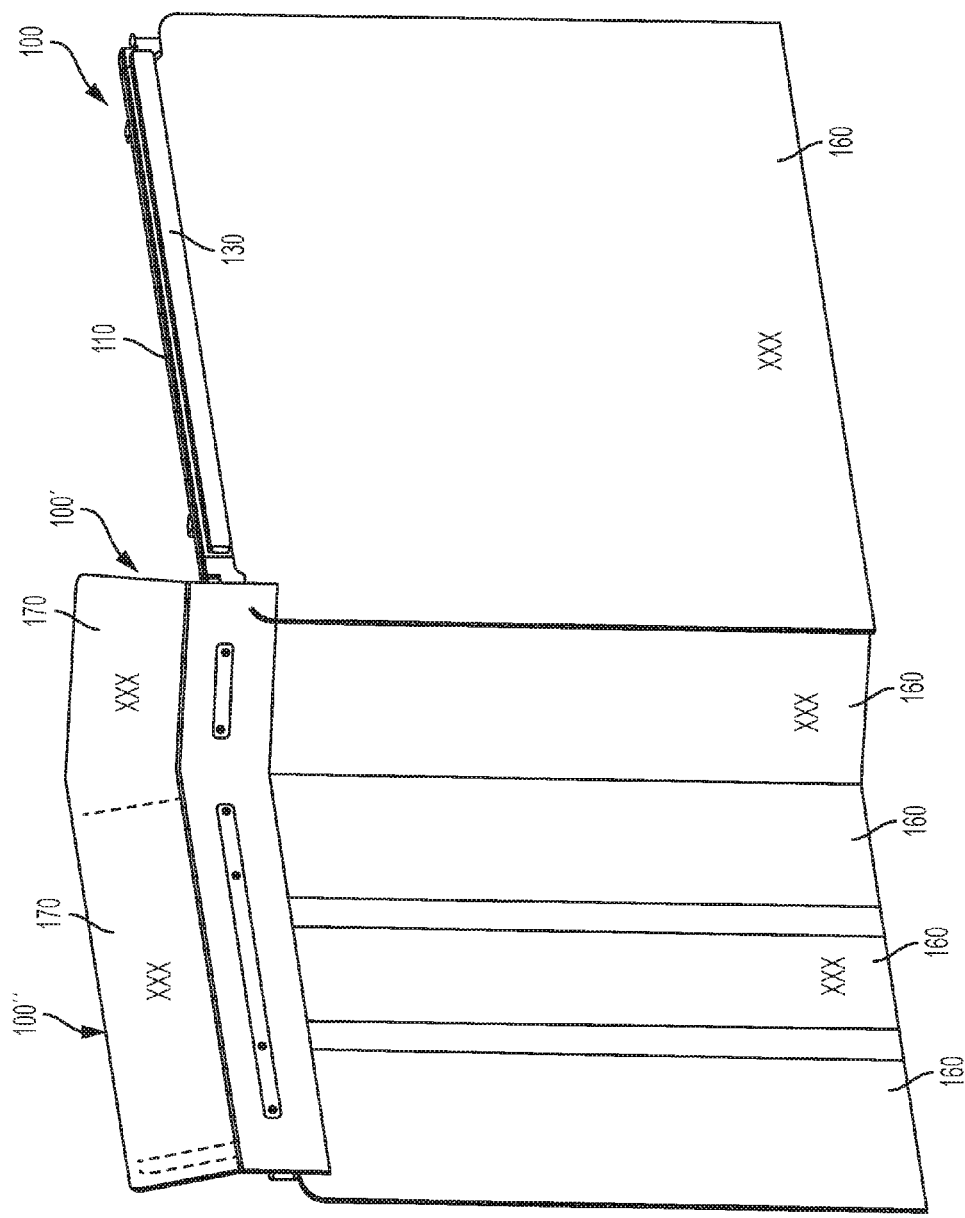

FIG. 1 shows a perspective view of a preferred embodiment of a radiation protection arrangement according to the present invention, FIG. 2 shows a perspective view of a further preferred embodiment of a radiation protection arrangement according to the present invention, FIG. 3 shows a side view of a preferred embodiment of a radiation protection arrangement according to the present invention, FIG. 4 shows a perspective view of a preferred embodiment of a radiation protection arrangement according to the present invention, FIG. 5 shows a perspective view of a preferred embodiment of a radiation protection arrangement according to the present invention, FIG. 6 shows a perspective view of of a preferred embodiment of a radiation protection arrangement according to the present invention, FIG. 7 shows a perspective view of a preferred embodiment of a radiation protection arrangement according to the present invention, FIG. 8 shows a perspective view of a preferred embodiment of a radiation protection arrangement according to the present invention, and FIG. 9 shows a perspective view of a preferred embodiment of a radiation protection arrangement according to the present invention.

FIG. 1 shows an embodiment of a radiation protection arrangement 100 according to the present invention for attachment to a treatment table. The radiation protection arrangement 100 comprises a holder 110 which can be fitted to a support rail of a treatment table (not shown). A radiation protection drape 160 is attached to the holder 110. The holder 110 further comprises a fastening device 120. According to the preferred embodiment of the present invention as shown in FIG. 1, the fastening device 120 comprises a first bracket part 121, a second bracket part 122, a third bracket part 123 and a fourth bracket part 124. The bracket parts 121, 122, 123, 124 are fastened to a long side of the holder 110, which in the mounted state point in the direction of the treatment table. The bracket parts 121, 122, 123, 124 have each an L-shaped profile with a first leg L1, L1', L1", L1'" and a second leg L2, L2', L2", L2'". As can be seen from FIG. 1, the first legs L1, L1' of the first bracket part 121 and the second bracket part 122 are aligned in parallel and the second legs L2, L2' of the first bracket part 121 and the second bracket part 122 face each other. The first bracket part 121 is arranged at an upper edge of the holder 110 and the second bracket part 122 at a lower edge of the holder 110. The first bracket part 121 is arranged relative to a longitudinal direction of the holder 110 at a first distance d from the second bracket part 122 such that the holder 110 in a first position in which the holder 110 is pivoted at an angle relative to the support rail can be brought into contact with the support rail and can be brought into a second position in which the holder 110 is mounted on the support rail by a pivoting motion.

According to the preferred embodiment of the present invention as shown in FIG. 1, the third bracket part 123 and the fourth bracket part 124 are arranged such that the first legs L1", L1'" of the third and fourth bracket parts 123, 124 are aligned in parallel and the second legs L2", L2'" of the first and fourth bracket parts 123, 124 point in the same direction, and the third and fourth bracket parts 123, 124 are arranged such that, in the fitted state, the first legs L1", L1'" rest on the support rail.

In the present embodiment, the distance n of the third bracket part 123 from the second bracket part 122 is 25 times the first distance d between the first bracket part 121 and the second bracket part 122. In the present embodiment, the distance of the fourth bracket part 124 from the third bracket part 123 is the same as the first distance d between the first bracket part 121 and the second bracket part 122.

On each of its short sides, the holder 110 has a first part 140 of an articulated joint. The first part 140 of the articulated joint comprises a bore 141 and a pressing device 142. The first part 140 of the articulated joint is suitable for being connected to a second part 150 of the articulated joint, which for example is attached to a holder of a second radiation protection arrangement, such that the first and second parts 140, 150 of the articulated joint form an articulated joint provided with multiple lock-in positions. The first part 140 comprises a bore 141 and a pressing device 142. The first and second parts 140, 150 of the articulated joint are discussed in detail in FIGS. 5 to 8 below.

Furthermore, the holder 110 comprises an additional rail 130 attached to the side opposite to the fastening device 120. The additional rail 130 is connected to the holder 110 by corresponding bolts 131 so that it is preferably slightly spaced apart from the holder 110. This spacing of the additional rail 130 from the holder 110 facilitates the potential placing of additional radiation protection shields, as shown in FIG. 9.

FIG. 2 shows a further embodiment of a radiation protection arrangement 100 according to the present invention for attachment to a treatment table. The radiation protection arrangement 100, just like the embodiment shown in FIG. 1, comprises a holder 110 which can be placed on a support rail of a treatment table. The embodiment shown in FIG. 2 differs from the embodiment shown in FIG. 1 in that the second legs L2", L2'" of the third and fourth bracket parts 123, 124 as well as the second legs L2, L2' of the first bracket part 121 and the second bracket part 122 face each other. The radiation protection arrangement 100 and/or the holder 110 is slid sideways onto the support rail without the holder 110 being pivoted relative to the support rail of the treatment table.

FIG. 3 shows a side view of a preferred embodiment of the present invention. The side view of the embodiment as shown in FIG. 3 corresponds to the side view both of the embodiment shown in FIG. 1 and the embodiment shown in FIG. 2.

Thus, at its long side facing the treatment table, the holder 110 comprises the fastening device 120 with the first and second bracket parts 121, 122, wherein the two bracket parts 121, 122 each have an L-shaped profile with the already discussed first and second legs L1, L1', L2, L2'. At the front side or the short side of the holder 110, there is arranged the first part 140 of the articulated joint, which comprises the bore 141 and the pressing device 142. At the long side facing away from the treatment table, the holder 110 comprises mounting bolts 131 on which the additional rail 130 is mounted. In view of the length of the bolts 131, the additional rail 130 is spaced apart from the holder 110.

FIG. 4 shows a perspective view of a radiation protection arrangement 100 according to the present invention for attachment to a treatment table. This preferred embodiment resembles the embodiment shown in FIG. 2. In particular, however, FIG. 4 shows again the additional rail 130 in its entirety.

FIG. 5 shows an embodiment of the first part 140 of the articulated joint according to the present invention. The first part 140 of the articulated joint is attached to the short side of the holder 110. The additional rail 130 as well as the protection drape 160 are likewise attached to the holder 110. There is further shown the pressing device 142 which according to the present embodiment comprises a ball-ended thrust screw. In addition, the first part 140 of the articulated joint comprises the bore 141. According to the present embodiment, a plain bearing bushing made from plastic, preferably PTFE, is arranged in the bore.

FIG. 6 shows an embodiment of the second part 150 of the articulated joint according to the present invention. Just like the first part 140 of the articulated joint, the second part 150 of the articulated joint can be attached to the short side of the holder 110, too. Likewise, the second part 150 of the articulated joint can be attached to an additional radiation protection shield without holder 110 so that the additional radiation protection shield or the additional radiation protection arrangement is not directly in contact with the treatment table. The second part 150 of the articulated joint comprises a head 152 and a bolt 151. The head 152 comprises a plurality of recesses 154. The bolt 151 of the second part 150 of the articulated joint can be inserted into the bore 141 of the first part 140 of the articulated joint. The recesses 154 of the head 152 of the second part 150 of the articulated joint are designed such that by inserting the bolt into the bore 141 the pressing device 142 is received in the recess 154. In the present case, the recesses 154 therefore have suitable passages at the side facing the bolt 151, so that when the bolt 151 is inserted into the bore 141, the pressing device 142 can be easily received in the recesses 154.

Furthermore, at its end opposite to the head 152 the bolt 151 has a chamfer facilitating insertion of the bolt 151 into the bore 141.

FIG. 6 shows a further embodiment of the second part 150 of the articulated joint according to the present invention. An angle of 0.75° lies between the bolt 151 and the main body of the second part 150 of the articulated joint. In other words, the bolt 151 is not parallel to the main body of the second part 150 of the articulated joint. This angle, preferably 0.75°, provides for a pretension at the bolt. This pretension ensures that, in the case of loading of the joint connection, for example by a free-standing end to a part 140, 150 of the articulated joint, the two radiation protection arrangements connected to each other by the articulated joint join up flush with each other.

FIG. 8 shows an assembled articulated joint comprising a first part 140 and a second part 150. It can clearly be seen that the pressing device 142 was received in a recess 154, while the other recesses 154 of the head 152 are not filled, and all recesses 154 together form a pattern so that predefined angular settings can be realized with the articulate joint having multiple lock-in positions.

By application of a predefined force which is exerted on the first part 140 it is possible to move the pressing device 142 from a first lock-in position where the pressing device 142 sits in a first recess 154 to a second lock-in position where the pressing device 142 sits in a second recess 154. In other words, the pressing device 142 can be moved from a first lock-in position to a second one by rotation of the articulated joint against a predefined force.

FIG. 9 shows an assembled system from a plurality of radiation protection arrangements 100, 100', 100" interconnected via the articulated joints as described in FIGS. 5 to 8, according to an embodiment of the present invention. Merely the right radiation protection arrangement 100 comprises a holder 110 and is attached to the treatment table, the radiation protection arrangements 100', 100" are connected to the radiation protection arrangement 100 without being directly connected to the treatment table. Furthermore, the radiation protection arrangements 100', 100" comprise plug-in radiation protection shields 170 which are attached to corresponding rails 130. With the articulated joints provided with lock-in positions it is possible to lock the positions of the radiation protection arrangements 100, 100', 100" at an angle predefined by the recesses 154. Consequently, the relative positions of the radiation protection arrangements 100, 100', 100" to each other can be maintained both when the treatment table is in an inclined position and when the radiation protection arrangements 100, 100', 100" are unintentionally jolted, e.g., by the operating personnel.

Although the invention has been represented and described in detail by means of the Figures and the corresponding description, this representation and this detailed description are to be understood as being illustrative and exemplary and not as limiting the invention. It goes without saying that persons skilled in the art can effect changes and modifications without leaving the scope and the spirit of the following claims. In particular, the invention also comprises embodiments with any combination of features mentioned or shown above or below with regard to various embodiments.

The invention also comprises individual features in the Figures even if they are shown in connection with other features and/or are not mentioned above or below. It is also possible that the alternatives of embodiments described in the Figures and the description and individual alternatives and their features are excluded from the subject-matter of the invention or from the disclosed subject-matters. The disclosure encompasses embodiments which solely comprise the features described in the claims and/or in the exemplary embodiments as well as embodiments which additionally comprise other features.

The invention claimed is:

1. A radiation protection arrangement for attachment to a support rail, which is attached to a side of a treatment table, comprising:
    a holder on which a radiation protection drape is arranged, the holder being attachable to the support rail and comprising a fastening means with which the holder can be fastened to the support rail,
    wherein the fastening means is formed on one side of the holder and comprises at least one first bracket part and at least one second bracket part,
    wherein each of the first and second bracket parts has an L-shaped profile with a first leg (L1, L1') and a second leg (L2, L2'),
    wherein the first and the second bracket parts are arranged such that the first legs (L1, L1') are aligned in parallel and the second legs (L2, L2') face each other, and wherein the first bracket part is arranged at an upper edge of the holder and the second bracket part is arranged at a lower edge of the holder, that the first bracket part is arranged relative to a longitudinal direction of the holder at a first distance from the second bracket part such that the holder in a first position in which the holder is pivoted relative to the support rail can be brought into contact with the support rail and, with a pivoting motion, can be brought into a second position in which the holder is attached to the support rail.

2. The radiation protection arrangement according to claim 1, wherein the fastening means comprises a third bracket part.

3. The radiation protection arrangement according to claim 2, wherein said third bracket part is arranged in a longitudinal direction of the holder at a second distance from the second bracket part, wherein the second distance is preferably n times greater than the first distance.

4. The radiation protection arrangement according to claim 3, wherein n is in the range of from 1.5 to 15.

5. The radiation protection arrangement according to claim 2, wherein the third bracket part has an L-shaped profile and/or comprises a fixing device.

6. The radiation protection arrangement according to claim 2, wherein the fastening means comprises a fourth bracket part arranged in longitudinal direction of the holder at a third distance from the third bracket part.

7. The radiation protection arrangement according to claim 6, wherein said fourth bracket part is arranged in longitudinal direction of the holder at a third distance from the third bracket part, wherein the third distance is m times greater than the first distance.

8. The radiation protection arrangement according to claim 7, wherein m is in the range of 0.5 to 15.

9. The radiation protection arrangement according to claim 6, wherein the fourth bracket part has an L-shaped profile and/or comprises a fixing device.

10. The radiation protection arrangement according to claim 9, provided the third and fourth bracket parts each have an L-shaped profile, wherein the L-shaped profiles of the third and fourth bracket parts each have a first leg ($L1''$, $L1'''$) and a second leg ($L2''$, $L2'''$), wherein the third and fourth bracket parts are arranged such that the first legs ($L1''$, $L1'''$) are aligned in parallel and the second legs ($L2'$, $L2'''$) show in the same direction and the third and fourth bracket parts are arranged such that, in the fitted state, the first legs ($L1''$, $L1'''$) of the third and fourth bracket parts rest on the support rail.

11. The radiation protection arrangement according to claim 1, wherein the holder further comprises an additional rail which is attached to the side opposite to the fastening means.

* * * * *